(12) United States Patent
Arenas Latorre et al.

(10) Patent No.: US 10,857,303 B2
(45) Date of Patent: Dec. 8, 2020

(54) MONITORING DEVICE FOR DRUG APPLICATION WITH A DRUG PEN, WITH LOGGING, COMMUNICATION AND ALARMS

(71) Applicant: INSULCLOUD, S.L., Madrid (ES)

(72) Inventors: Jesús Arenas Latorre, Madrid (ES); José Luis López Sánchez-Pascuala, Madrid (ES)

(73) Assignee: INSULCLOUD, S.L., Madrid (ES)

( * ) Notice: Subject to any disclaimer, the term of this patent is extended or adjusted under 35 U.S.C. 154(b) by 234 days.

(21) Appl. No.: 15/578,186

(22) PCT Filed: May 30, 2016

(86) PCT No.: PCT/EP2016/062196
§ 371 (c)(1),
(2) Date: Nov. 29, 2017

(87) PCT Pub. No.: WO2016/193229
PCT Pub. Date: Dec. 8, 2016

(65) Prior Publication Data
US 2018/0147362 A1 May 31, 2018

(30) Foreign Application Priority Data

May 29, 2015 (EP) .................................. 15382286

(51) Int. Cl.
*A61M 5/315* (2006.01)
*G06F 19/00* (2018.01)
*G16H 20/17* (2018.01)
*A61M 5/24* (2006.01)

(52) U.S. Cl.
CPC ..... *A61M 5/31551* (2013.01); *G06F 19/3468* (2013.01); *G16H 20/17* (2018.01); *A61M 5/24* (2013.01); *A61M 5/31585* (2013.01); *A61M 2205/215* (2013.01); *A61M 2205/3368* (2013.01); *A61M 2205/3553* (2013.01);
(Continued)

(58) Field of Classification Search
CPC ............ A61M 5/31551; A61M 5/3135; A61M 5/31566; A61M 5/31585; A61M 5/3157;
(Continued)

(56) References Cited

U.S. PATENT DOCUMENTS

2002/0096543 A1 7/2002 Juselius
2008/0262469 A1 10/2008 Brister et al.
(Continued)

FOREIGN PATENT DOCUMENTS

WO 99/02210 A1 1/1999
WO 2010/098927 A1 9/2010
(Continued)

*Primary Examiner* — Kevin C Sirmons
*Assistant Examiner* — Alexandra Lalonde
(74) *Attorney, Agent, or Firm* — Seed Intellectual Property Law Group LLP

(57) ABSTRACT

The present invention provides a device (1) for monitoring the application of a drug to a patient by means of a drug pen (100), whereby the drug pen comprises a front end provided with an injection needle and a rear end provided with an actuation pushbutton, the device comprising a body (2) which can be dismountably coupled to the pen; an injection detection means determining when a drug injection is carried out; and a processing means configured for storing the date and time of the injection when the injection detection means detects that a drug injection is carried out, whereby the body is configured to be coupled to the pushbutton of the pen such that the pushbutton is actuated by pushing directly on the body, whereby the injection detection means is implemented as actuation detector configured for detecting said pushing action.

24 Claims, 7 Drawing Sheets

(52) U.S. Cl.
CPC ............... *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/6081* (2013.01)

(58) Field of Classification Search
CPC .. A61M 2205/3368; A61M 2205/3553; A61M 2205/3561; A61M 2205/3584; A61M 2205/6081; A61M 5/24; A61M 5/20; A61M 5/3155; A61M 5/31548; A61M 5/31545; A61M 5/31533; A61M 5/3129; A61M 5/31; A61M 5/31565; A61M 5/31576; A61M 2205/3546; A61M 2205/3576; A61M 2205/6063; A61M 2205/52
See application file for complete search history.

(56) References Cited

U.S. PATENT DOCUMENTS

| | | | | |
|---|---|---|---|---|
| 2009/0043253 | A1* | 2/2009 | Podaima | G16H 10/60 604/67 |
| 2009/0194104 | A1* | 8/2009 | Van Sickle | A61M 15/00 128/203.12 |
| 2012/0053527 | A1* | 3/2012 | Cirillo | A61M 5/31525 604/189 |
| 2013/0197445 | A1* | 8/2013 | Schabbach | A61M 5/5086 604/189 |
| 2013/0245545 | A1* | 9/2013 | Arnold | A61M 5/1723 604/66 |
| 2014/0005950 | A1* | 1/2014 | Groeschke | A61M 5/31525 702/19 |
| 2016/0129182 | A1* | 5/2016 | Schuster | A61M 5/16831 702/56 |
| 2017/0286638 | A1* | 10/2017 | Searle | A61M 5/16804 |

FOREIGN PATENT DOCUMENTS

| | | | | |
|---|---|---|---|---|
| WO | 2012/127046 | A2 | 9/2012 | |
| WO | 2013/120777 | A1 | 8/2013 | |
| WO | 2013/120778 | A1 | 8/2013 | |
| WO | 2013/156510 | A1 | 10/2013 | |
| WO | 2014/037331 | A1 | 3/2014 | |
| WO | WO-2014037331 | A1 * | 3/2014 | ............... A61M 5/24 |
| WO | 2014/152704 | A1 | 9/2014 | |
| WO | 2015/136564 | A1 | 9/2015 | |
| WO | WO-2015136564 | A1 * | 9/2015 | ......... G06F 19/3456 |

* cited by examiner

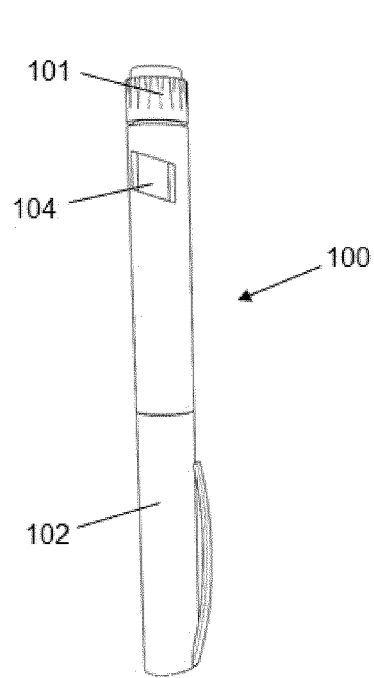
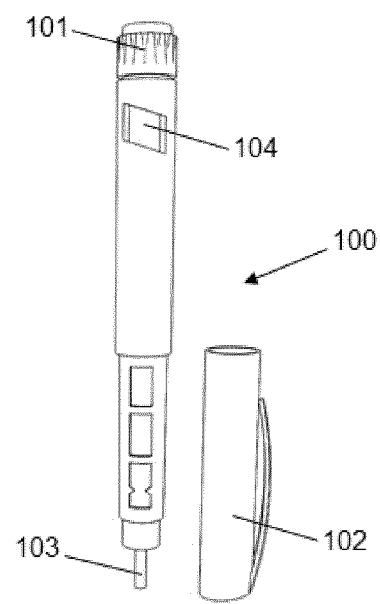
FIG. 1a  FIG. 1b

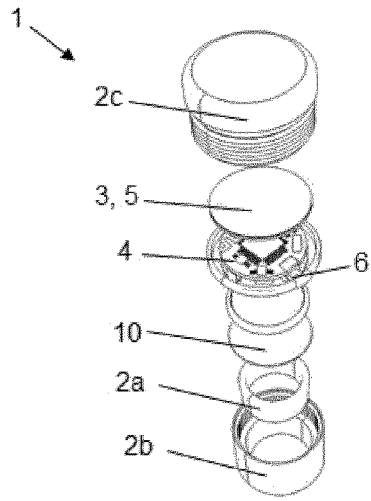
FIG. 2a
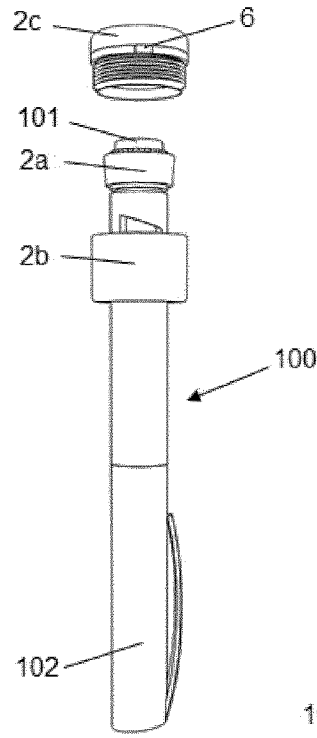
FIG. 2c
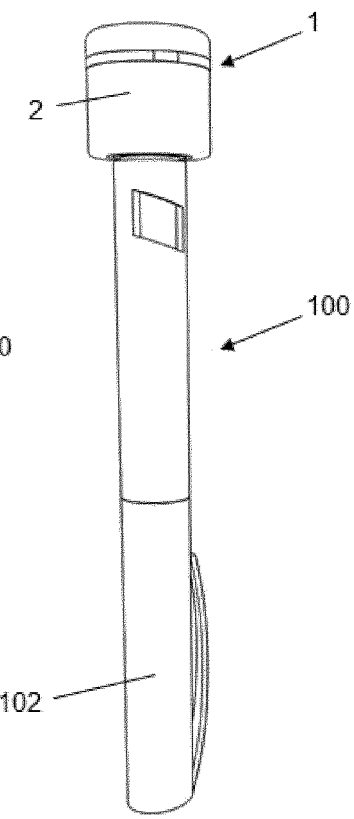
FIG. 2d
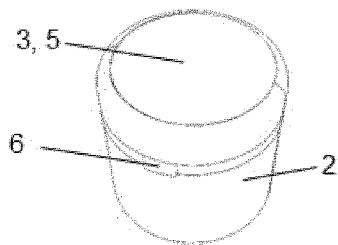
FIG. 2b
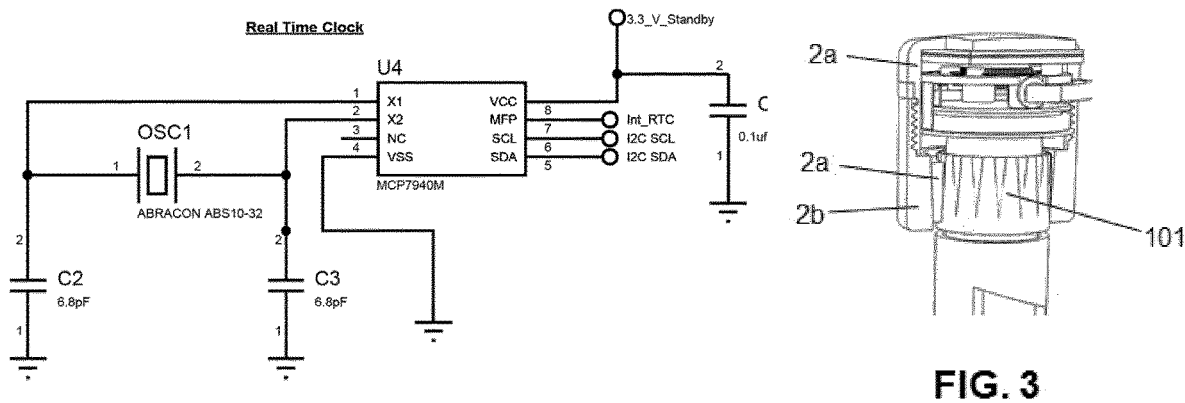
Fig. 2e
FIG. 3

MONITORING DEVICE FOR DRUG APPLICATION WITH A DRUG PEN, WITH LOGGING, COMMUNICATION AND ALARMS

OBJECT OF THE INVENTION

The present invention generally belongs to the field of medicine, and more particularly to the field of the means designed for ensuring an appropriate periodic application of a drug by chronic patients, such as the application of insulin in diabetic patients, in order to increase the adherence of the treatment and to improve the quality of life.

A first object of the present invention is a novel device designed to be coupled to a drug application pen of any type in order to provide the patient with information useful for controlling what kind of drug is injected, how much drug is injected, when it is injected. Further, the device is to enable monitoring of various parameters related to drug administration and application so that the treatment of the patient can be controlled by the patient himself or by caregivers, family members or doctors. It is a particular object of present invention to increase the adherence of the treatment with insulin injected by an insulin pen and to improve the quality of life of the patient.

A second object of the present invention is an operation method for the above-described device.

PRIOR ART

Diabetes mellitus comprises a number of metabolic disorders causing a chronic high glucose concentration in blood (hyperglycemia), mainly because of an insufficient secretion of insulin by the pancreas, diabetes type 1 or high periphery resistance to endogenic insulin diabetes type 2. Currently there are more than 485 million people with diabetes in the world, the insulin treatment has a high efficacy so one of the bigger challenges is increase the adherence of the treatment to avoid the severe problems due to an uncontrolled disease, this challenge exist in all chronic diseases.

Most diabetes patients are treated by means of periodic insulin injections. There exist a plurality of devices specially designed for the injection of insulin, although in connection with the present invention mention must be made to the so-called insulin injection pens. These pens are similar to a writing pen having a needle at one end and a pushbutton at the opposite end for actuating an insulin cartridge housed inside the body of the pen. When the patient pushes the pushbutton, a plunger pushes the cartridge for causing the injection of a predetermined amount of insulin through the needle. Each cartridge stores enough insulin for a number of injections, e.g. 300 units of insulin. When the cartridge is empty, it is discarded and replaced by a new full cartridge, or an insulin pen is replaced by a new, full insulin pen.

Although these devices allow for an easy and fast injection of insulin, the patient may forget what time a previous injection was carried out, the amount of insulin injected, whether a specific injection was in fact carried out or not, etc. Consequently, patients, their parents or tutors in the case of very young patients, or even the endocrinologist, are not certain about the evolution and data concerning said injections. This poses an important drawback, since the injection of an incorrect amount of insulin may have potentially serious consequences for the patient.

The same problem arises in connection with the injection of other drugs in chronic patients who must carry out injections several times a day. As an example, mention can be made to the injection of growth hormone in short persons, the GLP1 treatment in diabetic patients type 2, the injection of vitamins in persons with deficient iron absorption, the injection of heparin for preventing venous thrombosis, etc.

In order to solve this problem, there exist devices mainly consisting of a drug application pen having electronic means for controlling the injections. However, these devices are disadvantageous in that the electronic board is embedded in the pen, and therefore the users may not employ the pen they are used to. Further, these devices are complex and expensive.

Additionally, these devices are only useful for the patient carrying them and using them, that is, they do not allow for remotely checking the information in real time by means of external devices. This is important, since third persons such as parents, tutors or doctors may wish to check said information by means of devices such as tablets, smartphones or computers.

These problems are not only related with insulin in diabetic patients, but it is common in other chronic diseases using injection pens such as multiple sclerosis, fertility methods, etc.

DESCRIPTION OF THE INVENTION

The above drawbacks are addressed by the present invention disclosing a device capable of coupling to any model of drug application pen and having means for automatically detecting an injection and for communicating the patient information about the next injection. Specific features and advantages of the device of the invention will be apparent from the description included in the present document. The invention also discloses a method for operating the device.

In the present document, the term "drug" must be widely interpreted to encompass any substance periodically or repeatedly injected into the body of a patient. Specially, the device of the invention is useful for monitoring the injection of drugs in chronic patients, and more particularly for diabetes patients who must receive insulin injections several times a day. However, the term "drug" not only refers to insulin, but also to substances such as GLP1, growth hormone indicated for short persons, vitamins indicated for persons with deficient iron absorption, heparin indicated for persons prone to venous thrombosis, ovarian stimulation substances indicated for persons under in vitro fecundation treatment, as well as other substances indicated for patients with allergies or multiple sclerosis. However, it turned out that in a preferred embodiment, the device is to be used advantageously with insulin.

The term "pen" or "drug pen" refers to a device designed for the injection of drugs in chronic patients. It is an elongated device having a writing pen-like shape comprising a front end having an injection needle and a rear end having an actuation pushbutton. The pen further has a cap, similar to those of conventional writing pens, with a cavity for coupling the front end of the pen in order to cover the injection needle. Some rechargeable pen models housing a disposable cartridge storing the drug have the actuation pushbutton displace a plunger pushing the drug in the cartridge towards the injection needle. Other pen models are wholly disposable, that is, they are discarded when an embedded inner drug reservoir is empty.

A first aspect of the invention discloses a device for monitoring the application of a drug to a patient using a drug pen, the device mainly comprising a body, an injection detection means, and a processing means. These elements are now disclosed in detail:

a) Body

The body can be dismountably coupled to the drug pen. The term "dismountably" refers to the fact that the body may be coupled and uncoupled from the pen several times without causing any damage to the pen. In principle, the body may be configured in a number of ways provided it can be coupled and uncoupled to any existing pen in the market. In this context, it is important that the body to be coupled to the pen be universal, that is, it be suitable for any pen in the market. The device according to the present invention is compatible with a large amount of commercially available pens such as e.g. Kwikpen, flexpen and Solostar.

b) An Injection Detection Means

This detection means serves to detect that a drug injection is carried out. This detection occurs automatically, that is, the patient does not need to carry out any additional operation further than the usual steps he/she follows when carrying out a drug injection. To this end, the injection detection means is implemented as an actuation detector configured for detecting an actuation of the pen. An actuation detector comprises e.g. a mechanical button provided at the device. The skilled person will be able to recognize also different kinds of actuation detectors, i.e. detectors to detect actuation preferably of the pushbutton of the pen to carry out an injection.

c) A Processing Means

The processing means is configured for storing the date and time of the injection when the injection detection means detects that a drug injection is carried out. Preferably, the processing means is configured for storing a dataset including at least the date and time of the injection when the injection detection means detects that a drug injection is carried out. In order to do this, the processing means is in communication with the injection detection means; additionally, the processing means may further be configured for informing the patient as to when the next drug injection must be carried out, preferably via a wireless communication means and an external device. Further, the processing means may request information from the patient by means of several means such as screens, buttons, via a wireless communication means and an external device, and/or links to an external application. Based on said information, the processing means can warn the patient that an injection must be carried out.

The device preferably comprises a real time clock, i.e. a clock adapted to output the date and time of day, connected to the processing means such that the processing means is adapted to store a dataset including at least the date and time of the injection.

In a preferred embodiment, the device is provided with drug kind detection means adapted to detect the kind of applied drug, preferably of applied insulin. In a further preferred embodiment, the device comprises a dosage detection means adapted to detect the amount of charged drug, preferably insulin. A corresponding problem solved by the present inventors in this respect is to find a way to detect what kind of insulin and how much insulin has been injected for various different insulin pens. By incorporating dedicated sensors into the device, it became possible to ensure compatibility with various pens such as e.g. Insulclok, Kwikpen, Flexpen, Solostar and Flextouch. Achieving this goal has been a challenge which was solved by the inventors by the provision of a combination of different sensors, specific software and calibration.

In the following, a specific configuration of the device to be coupled to the rear end of the pen where the actuation pushbutton is located is disclosed.

CONFIGURATION EXAMPLE

In the following configuration example, the body is configured to be coupled to the pushbutton of the pen such that the pushbutton is actuated by pushing directly on the body. Since the injection detection means is itself implemented as actuation detector, preferably as mechanical button, the injection detection means is configured for detecting said push on the body and hence for determining when a drug injection is carried out. That is, since the body is coupled to the pushbutton, when the user pushes the pushbutton for carrying out an injection said action is detected by the device of the invention and interpreted as an injection.

In a preferred embodiment, the processing means is adapted to detect the kind of drug, preferably insulin, at the time of injection. Preferably, to this end, the device comprises a drug kind detection means which preferably comprises a color sensor. As the skilled person will understand, usually, for example insulin pens have their own characteristic color in the rear push button. By providing the drug kind detection means, i.e. preferably the insulin kind detection means, with a color sensor such as e.g. a RGBW Color Sensor with I2C Interface—VEML6040A3OG, it becomes possible to detect the brand and the kind or type of insulin. As the skilled person will further understand, e.g. insulin dosage is typically adjusted by rotating a corresponding member provided at a standard insulin pen. Depending on the insulin kind or brand, the step of rotation will be different for the dosage. Thus, detecting the kind of drug by the device advantageously allows to store the kind of applied drug and dosage.

In a preferred embodiment of the invention the body comprises:

An essentially frustoconical gasket having an orifice configured for housing therein the pushbutton of the drug pen. The gasket may be made of any suitable material, such as for example rigid plastic.

A coupling portion having a through orifice configured for housing therein the gasket such that a compression takes place, said gasket being compressed firmly around the pushbutton.

A cover portion configured for being coupled to the attachment portion, the injection detection means implemented as actuation detector, i.e. for example as mechanical button, being provided in said cover portion.

Thanks to this coupling system, the device can be adapted to different types of drug pens merely by providing a plurality of gaskets with different shapes and internal diameters. Indeed, the main differences between different drug pen models in connection with the coupling of this configuration of the device are basically differences in diameter and/or shape of the pushbutton. By providing a set of gaskets of different shapes and internal diameters, a correct coupling of the device of the invention to any pen model is achieved.

On the other hand, since the injection detection means is located in the cover portion, and more particularly on the surface of the cover portion to be pressed by the patient when normally actuating the pushbutton, the device of this configuration automatically detects when an injection is carried out when the user normally pushes the pushbutton.

In a preferred embodiment of the invention, the injection detection means is implemented by a mechanical button provided in the cover portion. Preferably, the button may be configured for covering completely the upper surface of the cover portion. For example, the button may be in electrical communication with the processing means for opening or closing a contact depending on whether it is pushed or not, such that the processing means immediately receives the information as to whether a drug injection is carried out. An important advantage in connection with the use of a mechanical button as an injection detection means is the power savings in comparison with the use of electronic injection detection elements, since the operation and monitoring of the latter require an electrical power source.

According to the invention, when the device of the invention detects a drug injection by the patient, the processing means stores, preferably into a storage means of the device, the date and time of the injection, preferably in a storage means provided at the device. Preferably, when the device of the invention detects a drug injection by the patient, the processing means stores a dataset including at least the date and time of the injection.

As will be explained below, the device is preferably adapted to store various further parameters in the dataset in addition to the date and the time of drug application. Parameters are selected from the group of kind of applied drug, preferably kind of applied insulin, temperature of drug upon application, preferably temperature of insulin upon application, applied dose of drug, preferably of insulin, and orientation of the pen at the time of application. As the skilled person will understand, further parameters that are deemed helpful for assisting drug application and/or monitoring drug application can be included in the dataset.

Storing of a dataset of these parameters in combination with the time and date allows storing of a history of treatment. The dataset can be readout from the device e.g. using a wireless communication means and an external device such as a smartphone or personal computer. Dedicated software provided at the external device enables subsequent use of the dataset e.g. for building graphs, statistical data, etc. As the skilled person will understand, such treatment history is of particular advantage e.g. for a doctor to appropriately control the patient treatment. Providing the treatment history in this form as electronically recorded dataset is advantageous in that the patient is no longer required for example to manually write drug application data into a corresponding paper notebook. In addition, correctness of the data is ensured, i.e. the data cannot be falsified on purpose or unintentionally. Thus, by providing all of these parameters in combination, a particular advantage can be achieved as each one of these parameters is important to achieve an optimal treatment. In addition, in order to enable the device to be capable of storing all of these parameters, it was necessary to construct a device and to find corresponding sensors for each parameter so that the device housing all of these sensors could still be small enough to be coupled to a standard size drug pen such as an insulin pen and could still be conveniently used by a patient.

The date and time of injection, i.e. drug application, and/or the dataset can be readout from the device via wireless communication using an external device such as a user equipment, i.e. for example a mobile device such as a smartphone, a tablet, a laptop or a personal computer. To this end, in a preferred embodiment, the device further comprises a wireless communication means configured for communicating with an application installed in an external device. This communication means may be implemented in different ways, such as for example by means of Machine to Machine communication, Bluetooth, WiFi, WiMax, and others. The external device can be of any type such as a user equipment, i.e. a smartphone or mobile phone, a tablet, a computer, and the like. The external device can alternatively or in addition be a server or a group of servers. In any case, as disclosed in detail below, the most preferred configuration entails the communication with a smartphone through Bluetooth. Thus, preferably, the wireless connection is a Bluetooth connection. Preferably, via the communication means, data and parameters such as a desired time of the day for drug application can be inputted by the user using e.g. a smartphone or tablet.

In a preferred embodiment, in addition to storing the date and time of the injection, the device is adapted to store the date and time, preferably the dataset, on at least one external server. As the skilled person will understand, such external server or multiple external servers can form a so called "data cloud" which is a logical storage space provided for a user on such server or on such group of servers which may be provided by a hosting company or the like. The data cloud can be accessed via a general network such as a local communications network provided at home or in a hospital or via the internet. Preferably, the device is adapted, i.e. comprises the mentioned wireless communication means, to wirelessly access the general network, preferably the internet.

In a preferred embodiment, the device is adapted to store the date and time of the injection, preferably the dataset, on at least one server when, or as soon as, the device is connected to the general network, preferably to the internet. In an alternative or additional embodiment, the dataset can be communicated to the at least one server via a wireless connection (e.g. Machine to Machine communication or a Bluetooth connection) to a user equipment such as a smartphone, the user equipment being connected to the at least one server via the internet.

In addition to the above described functionality to store a dataset based on various parameters, the device is preferably adapted to warn or remind the user under certain circumstances based on the parameters. Thus, in a preferred embodiment, the device of the invention further comprises an alarm means for notifying the patient of certain events. The alarm means may be an acoustic means, visual means, vibration means, etc. As visual means, for example, an LED may be provided. For example, the device may output an alarm at a certain time of day to remind the user to use the pen to apply a drug. In other words, the patient can e.g. program the device for a number of daily injections and the alarm means will warn him/her at the appropriate time. Such programing can be accomplished via input of suitable data by the user through an external device such as a smartphone or tablet wirelessly connected to the device.

In a preferred embodiment, based on the stored date and time of the injection, the alarm means is adapted to output an alarm if a further injection is detected in a predefined time period following the stored date and time of the injection. The predefined time period may be a period of several hours, a day or any other suitable time period between necessary drug injections. Accordingly, a patient is warned immediately if he or she attempts to inject a drug too early such that an unnecessary injection can be avoided or at least the patient can be made aware of the fact that the second injection was too early. Thus, if the user has injected insulin and again wants to inject the same insulin, the device may e.g. output a continuous beep and an LED alarm light will turn red. Thus, the user is warned and informed that the user should not inject insulin.

Further, based on the detection result of the drug kind detection means, the alarm means are preferably adapted to warn a user if the user attempts to inject a wrong kind of drug, preferably insulin, for instance fast acting insulin instead basal insulin. Thus, if the user has injected insulin and again wants to inject the same insulin, the device may e.g. output a continuous beep and an LED alarm light will turn red.

In a preferred embodiment, the alarm means is adapted to cooperate with the wireless communication means to transfer an alarm to the external device preferably via the at least one external server. For example, in the above case of warning the user of a second, unnecessary injection, a message can be sent to a mobile device and the mobile device can e.g. display to the user: "You've already put this type of insulin. Are you sure you want to inject the insulin again?". Further, in the above example of informing the user of a wrong kind of insulin, a message may be sent to the mobile device which in turn may display "Insulin that you need is "X" and you're trying to put insulin "Y"—are you sure you want to inject this insulin?" In such cases that alarms are output to a user, the user may cancel the alarm e.g. by pushing a corresponding button on the device and may continue with the injection.

For example, the alarm means and the wireless communication means can be adapted such that an alarm message is sent to a remote person, i.e. a person different from a patient using the device, such as a doctor, a tutor or a family member via Machine to Machine communication or Bluetooth communication when the device has not been used for a preset time period after a preset date and time. Alternatively or in addition, the alarm means and the wireless communication means can be adapted such that an alarm is communicated to the at least one server which in turn is adapted to automatically sent a message such as an SMS, an email or a prerecorded telephone call to said person. To this end, the at least one external server is preferably provided with a corresponding software program.

In combination with the alarm means, the device is preferably provided with a charge state detecting means that is adapted to detect and monitor a charge state or filling state or filling level, of a drug cartridge of the drug pen or of a drug pen without pen. Based on a detection result of the charge state detecting means, the alarm means is preferably adapted to output an alarm when the charge state is below a predetermined threshold. For example, the threshold may be a minimum charge necessary for the application of a dose necessary for one injection. Thereby, mistakes and omission of drug application can be avoided. Thus, based on a detection result of the charge state detecting means, triggered by the alarm means, a message can be sent to a mobile device causing the mobile device to display "Insulin pen finished. Replace it by a new pen".

The device may also request additional information from the patient e.g. through a screen of an external device, for example the amount of drug injected. For example, in the specific case of insulin, the patient may be requested to indicate the amount of insulin injected and the glucose level at that time. This information, along with the information related with the date and time of each injection, can be stored in the storing means either embedded in the processing means or connected thereto, and it can subsequently be used for building graphs, statistical data, etc.

The wireless communication means, on one hand, allows for sending from the device of the invention both the dataset obtained automatically in connection with the date and time of each injection to the external device. The dataset is preferably processed into information accessible by the patient or the doctor, is converted into a convenient table, into graphs or the like. This function allows the patient to check all the information more conveniently in the external device.

After the data is sent to the external device, the data can be processed by a dedicated application on the external device. Alternatively, or in addition, the dataset is processed via a program installed on the at least one server using the dataset stored on the at least one external server. Information resulting from processing the dataset via the cloud service can be acquired by the external device e.g. via the internet. The external device can then display the information to the user of the device e.g. using a dedicated program or application installed on the external device. The data included in the dataset is processed to be accessible to the data, i.e. output of sensors that may be comprised by the device such as temperature sensors, orientation sensors (e.g. accelerometers) or the like, is processed into output such as numbers included in tables or graphs that can be displayed by the external device using dedicated software or applications. The dataset thus becomes accessible and understandable to the user.

Storing and/or processing of the data via the at least one external server enables synchronizing the treatment history among various external devices such as multiple smartphones e.g. of a parent and of a doctor. Thus, when the patient is e.g. a child, the data can be accessed via a mobile phone of a parent and at the same time via a mobile device or personal computer of a doctor. Thereby, control of the treatment e.g. of a child can be ensured. Similarly, if the patient is an elderly person, family members and a doctor can access cloud data such that treatment can be ensured by multiple persons.

On the other hand, the communication can also take place in the opposite direction, that is, from the application installed in the external device towards the device of the invention. In this case, the communication allows for carrying out configuration adjustments, programming the date and time of the daily programmed injections, requesting specific data such as graphs or the like, updating the software, etc.

In addition to the date (e.g. the day, month and year) and the time (e.g. the time of day), in a preferred embodiment, the dataset includes the temperature of the drug, preferably of the insulin, at the time of injection or application. To this end, the device is provided with means for detecting the drug temperature, i.e. for example a temperature sensor and corresponding electronics (e.g. ±0.5° C. Maximum Accuracy Digital Temperature Sensor—MCP9808T-E/MC to continuously monitor the temperature of the drug, preferably insulin), at the time of application which is connected to the processing means which in turn is adapted to store the temperature in the dataset. When designing the device, the inventors noted that the necessary drug dose to be applied can depend on the drug temperature. For example, in the case of extreme temperature the insulin can lose the efficacy. Thus, storing the drug temperature at the time of application is advantageous for later evaluation of the treatment. In addition, in a preferred embodiment, the alarm means is adapted to warn the user of the pen in the case that at the time of application, the detected drug temperature is above or below a preset threshold.

Further, in a preferred embodiment, the device further comprises a drug, preferably insulin, kind detection means adapted to automatically detect the kind of applied drug, preferably insulin, when a drug injection is detected, the drug kind detection means being connected with the processing means such that the processing means is adapted to store the kind of applied drug into the dataset.

It turned out that such drug kind detection is of particular advantage in the case of insulin. As the skilled person will understand, various kinds of insulin can be identified via a color label provided e.g. at the pushbutton of the pen. By providing an insulin kind detection means in the form of a color sensor with corresponding LED it turned out that this kind of sensor can be housed in the device of the invention while allowing the device to be suitably connectable to a standard size pen. At the same time, a very reliable insulin kind detection could be achieved while a combination of LED and color sensor is also energy efficient.

In a preferred embodiment, the drug is insulin and the drug kind detection means are adapted for automatic detection of the applied insulin.

In a preferred embodiment, the device further comprises a dosage detection means that is adapted to detect the amount of charged drug based on the setting of a dosage actuator provided at the pen. As the skilled person will understand, a drug pen such as an insulin pen is provided with a dosage actuator, e.g. a ring provided at the pen, which can be accessed by the user to set the desired dose. The dosage detection means is e.g. adapted to detect the setting of such dosage actuator to determine the dosage applied at the time of injection. The processing means is further adapted to store the amount of dosage applied into the dataset. Providing the dosage amount as one of the parameters included in the dataset enables e.g. later evaluation of the treatment and/or verifying correctness of the treatment.

In a preferred embodiment, the device further comprises a pen orientation angle detection means, which is adapted to detect the orientation angle of the pen at the time of drug application, whereby the processing means is adapted to store this orientation angle of the device in the data set. The parameter orientation angle is an angle of the device e.g. with respect to a normal environment such as a room or the like. An output of the pen orientation angle detection means can thus be an angle with respect to a room floor such that it can be detected if the pen has been held e.g. horizontal at the time of carrying out the injection.

By providing the pen orientation detection means it becomes thus possible to verify that the pen has been held at an expected orientation when the drug was applied. In other words, it would be expected that the pen is held approximately horizontally when applying a dose of insulin into a patient's belly. If the pen is held approximately perpendicular at the time of drug application, it can be assumed that the drug was not appropriately administered to the patient or was applied into the air. This enables e.g. a parent or a tutor to control appropriate drug application of a child or of a patient in need of assistance. For example, the parent may check the dataset stored at a particular time when the drug should be applied using a mobile phone even from a remote position. With the additional orientation information, the parent can ensure that the drug is in fact applied in an appropriate way. In a preferred embodiment, the pen orientation angle detection means comprises at least one accelerometer.

In a preferred embodiment, the device is provided with a battery charge state detection means adapted to detect the battery charge state of a battery of the device. Based on an output of the battery charge state detection means, the alarm means is adapted to output an alarm when the battery state is below a predefined threshold. For example, triggered by the alarm means, a message can be sent to a mobile device such that the mobile device is triggered to display "Insulclock very low battery, charge it please".

In a preferred embodiment, the device is provided with a failure detection means that is adapted to recognize if at least one sensor or detection means of the device does not work. For example, the failure detection means is preferably adapted to detect if the drug kind detection means does not output a detection result. Similarly, the failure detection means is preferably adapted to detect if the temperature sensor does not output a detection result.

Based on a detection result of the failure detection means, the alarm means is adapted to output an alarm if a failure is detected. For example, triggered by the alarm means, a message can be sent to a mobile device such that the mobile device is caused to display "Error of Use/Maintenance Insulclock, please remove your Insulclock pen and contact your call center, educator/endocrine service to send message to aa@insulclock.com".

In the following, further exemplary cases and exemplary alarms are described. For example, a continuous beep and orange LED can be an alarm to inform the user about low battery. If the battery charge is detected to be e.g. less than 10%, an alarm message may be triggered by the alarm means and displayed at the mobile device "Low battery Insulclock (less than 10%). Please charge your Insulclock".

Based on an output of the charge state detection means, the alarm means is preferably adapted to output an alarm if the drug pen has only two more doses. In this case, the alarm means may be adapted to trigger sending a message to the mobile device which is in turn caused to display a message "Insulin pen running low. Do not forget to bring a new one to replace the pen".

The device is preferably adapted to detect erroneous use of the insulin pen. For example, a case may occur that the user injects insulin, but stops pressing the device prematurely (e.g. before the piston has stopped and a time of e.g. 10 seconds has elapsed). It is known that mistakes can be caused if the user injects insulin, stops continuously pushing the button and presses the plunger several times. Therefore, in a preferred embodiment, the device is adapted such that an alarm is output if no or a wrong dose is applied or the injection is uncompleted.

To this end, based on an output of the actuation detector and the real time clock, the alarm means is adapted to output an alarm if actuation of the actuation detector is interrupted before a predefined time period after the date and time of the injection has passed. The predefined time period may be e.g. 10 seconds. Thus, if the user presses the pushbutton to start the injection, the time and date of the injection are recognized and stored. If the pushbutton is released before the predefined time period has elapsed, e.g. before 10 seconds have passed, this is recognized by the processing means based on an output of the actuation detector. Based thereon, the alarm means is adapted to output an alarm. For example, two short beeps and orange LED light may be output. Alternatively or in addition, a message may be triggered by the alarm means to be displayed at the mobile device "Injection unfinished. Continue to hold the device until you hear a continuous beep and the LED turns green".

When the user injects the insulin on time, the pen must not be removed from the body and the plunger shall be pressed until the LED turns green. Thus, in the case of correct application, the alarm means may be adapted to confirm such correct application by outputting two short beeps and green LED. A message may be triggered by the alarm means "Injected insulin. OKAY".

In a preferred embodiment, based on an output of the real time clock, the alarm means is adapted to output an alarm if a preset alarm time (a predefined date and time, or a time on each day, e.g. 9:00) is reached. Such alarm time may be input into the device using standard input means as they will be known to the skilled person. For example, a screen may be provided at the device and the alarm time may be input by corresponding buttons and verified through the screen. The input may also be accomplished using an external device such as a mobile phone. Alternative input means will be apparent for the skilled person. When the alarm time is reached, the alarm means may e.g. output an intermittent beep for a preset number of seconds and an orange LED may light up.

In a preferred embodiment, based on an output of the real time clock, if no injection has been detected based on an output of the actuation detector for a preset time period after the alarm time, the alarm means is adapted to trigger an alarm message.

For example, if one hour has passed after the alarm time and no injection has been detected, a message is automatically sent for example to a tutor, a doctor or caregiver. This message can be an e-mail sent from the server. The message can also be an SMS or a prerecorded telephone message to the caregiver.

The device as described above is of particular advantage as it preferably allows to automatically detect the dosage and the kind of insulin injected by the patient. This greatly increases the adherence of the treatment and improves the quality of life for the patient.

The operation of the device of the invention will be better understood from the following description of preferred embodiments.

BRIEF DESCRIPTION OF THE DRAWINGS

FIGS. 1a and 1b show an example of conventional insulin pen.

FIGS. 2a-2e show several views of an example with screen of a device according to the present invention.

FIG. 3 shows how the device of the invention is coupled to the pushbutton of an insulin pen.

PREFERRED EMBODIMENTS OF THE INVENTION

Figures 4A, 4B, 4C:
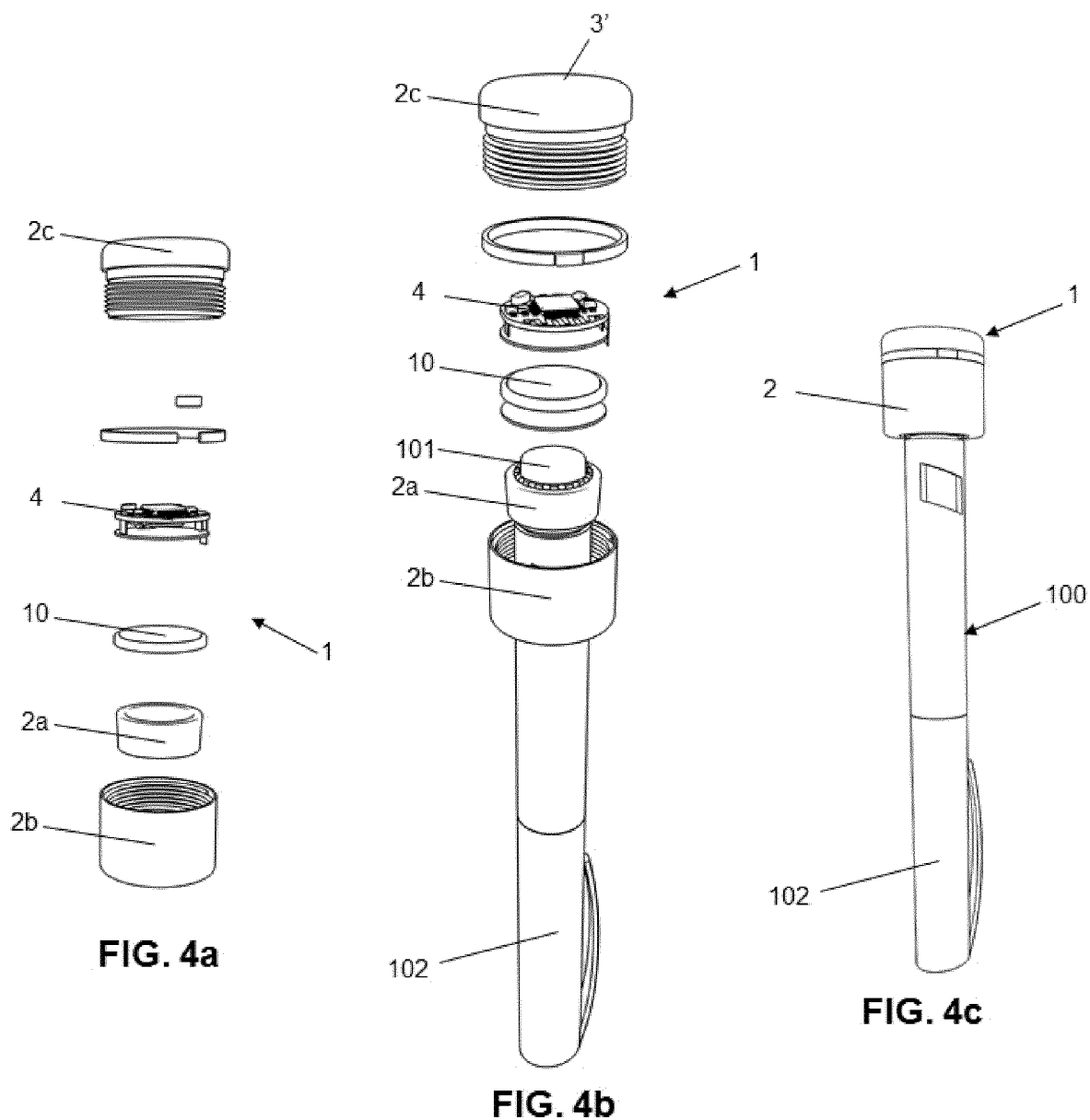
FIGS. 4a-4c show several views of an example without screen of the device according to the present invention.

A number of preferred embodiments of the present invention are now disclosed with reference to the drawings. The examples described here are specifically directed to the injection of insulin by an insulin pen in diabetic patients. However, as previously mentioned in this document, the invention must not be interpreted to be limited to insulin pens, as it is applicable to pens intended for the injection of any type of drug. Additionally, the present examples are exemplarily directed to disposable pens.

FIGS. 1a and 1b show the components of an example of a disposable conventional insulin pen (100). The pen (100) has an essentially cylindrical main body housing an insulin cartridge. An injection needle (103) is located at a front end of the body of the pen (100) for injecting the insulin stored in the insulin cartridge. In order to do so, the patient pushes a pushbutton (101) located at the rear end of the body of the pen (100) this pushbutton has an unique and characteristic color for each kind of insulin and insulin pen, the pushbutton (101) in turn actuating an inner plunger that actuates the cartridge for injecting the insulin through the needle (103). Before being actuated, the pushbutton (101) is retracted by turning it backwards a distance in proportion to the insulin dose to be injected. As the user turns the pushbutton (101), an indication window (104) shows the user the number of insulin units that is being charged for injection. A cap (102) covers the front end of the pen (100) for preventing accidents with the needle (103).

As disclosed below, the device (1) of the invention is specially designed for being coupled to any model of insulin pen (100) of this type and for automatically detecting when the patient carries out an injection.

The device (1) for monitoring the application of insulin is specifically designed to be coupled to the pushbutton (101) of the insulin pen (100). The detection means (3, 3') is provided in the device (1) such that it is activated by the pressure exerted by the patient when pushing the pushbutton (101) of the insulin pen (100). To this end, the injection detection means is implemented a actuation detector configured for detecting a pushing action on the pushbutton. A configuration of the device (1) of the invention is shown in detail in FIGS. 2a-2e.

This device (1) comprises a body (2) formed by a coupling portion (2b), a cover portion (2c), and a gasket (2a). The gasket (2a) has an essentially frustoconical hollow shape configured for accommodating therein the pushbutton (101) of the conventional insulin pen. Coupling portion (2b) has an essentially cylindrical shape with an inner orifice whose diameter is similar to that of the gasket (2a), such that it can slide along the main body of the insulin pen (100) itself. As shown in FIG. 2c, the coupling portion (2b) is displaced vertically upwards until the gasket (2a) is housed therein. During this process, the coupling portion (2b) compresses the gasket (2a) such that said gasket (2a) strongly embraces the pushbutton (101) for achieving a firm attachment thereto. Next, cover portion (2c) is coupled to the coupling portion (2b), in this example by means of a threaded connection, the three parts forming a single rigid body housing the rest of the components of the device (1).

The gasket (2a) may be provided with different shapes and internal diameters for being coupled to the pushbuttons (101) of different pen (100) models. Thus, the present device (1) may be used with any insulin pen (100) model.

In the shown example, a touchscreen (3, 5) is provided in the uppermost portion of the body (2). Since the device (1) of the invention is coupled to the pushbutton (101) of the pen (100), the pushbutton (101) itself being hidden inside the body (2), when using the pen (100) the patient pushes directly the upper portion of the device (1) which is detected by an actuation detector being connected with the pushbutton or implemented as the pushbutton. The actuation detector can be configured such that a prolonged push is interpreted as an injection for using it as an injection detection means (3).

In the present example, the screen (5) is a monochrome multipixel 100×100 pixel screen. A touch panel having a matrix of about 20×20 pressure points is provided on the screen (5). The control unit of the screen may be provided separately or else it may be embedded in the processing means (4). A small lateral button (6) connected to the screen (5) protruding through the cover portion (2c) allows the patient to confirm the data introduced through the touchscreen (5).

The device comprises a processing means (4) which, in this example, is located under the screen (5). The processing means (4) may in principle be implemented in a number of ways, such as for example by a microcontroller, a microprocessor, etc. In any case, whether embedded in the processing means (4) or as a separate element connected thereto, the device (1) comprises a control clock for controlling the date and time. An example circuit diagram of a suitable real time clock or control clock is depicted in FIG. 2e. This example circuit is a I2C™ Real-Time Clock/Calendar with SRAM—Chip MCP7940MT-I/MNY and allows to generate data on the time and date (month/day/year). Additionally, the device (1) also comprises, either embedded in the processing means (4) or as separate elements connected thereto, a communication means, a storing means, and an alarm means.

The storing means allows for storing the information obtained by the device (1), either automatically through the detection of injections, or else manually through the data requested to the patient by means of the touchscreen (5), the operation program, temporal operation data, etc. In this specific example, a ROM is used for the operation program, a static memory stores the different elements of the database, alarms, etc., and a RAM stores temporal operation data such as variables or counters.

The communication means allows for sending the information obtained and stored in the device (1) to an external device, such as for example a smartphone, a tablet or a computer. In this specific example, the communication means is a Bluetooth chip using a low consumption communication protocol, such as for example protocols 3.0 or 4.0 onwards. On the other hand, the external device has an application, or app, specifically designed for managing the device (1) installed therein. The patient or other person, such as a tutor or a doctor, will be able to view the information stored by the device (1) not only in the touchscreen (5) but also by means of the smartphone, tablet or computer. In addition to viewing the information, the patient can change configuration data of the device (1), such as date and time of the alarms, etc.

The alarm means will warn the patient of an upcoming insulin injection. The alarm means may be implemented in several different ways, but this example uses a small buzzer.

A small battery (10) supplies power to the different electronic devices of the device (1) of the invention.

FIGS. 4a-4b show a further example. In the figures, the same numerals refer to similar elements in the first version. In the example, the actuation detector is implemented as a mechanical button (not explicitly shown in the figures). For example, the button may be provided on the electronic board where the processing means (4) is located such that actuation of the button (101) causes an electrical contact to close. In any case, the device (1) mechanically detects a push of the button (101) of the conventional pen (100).

In the following, further features are described which can be used in combination with all of the above described preferred embodiments.

Figures 5A, 5B:
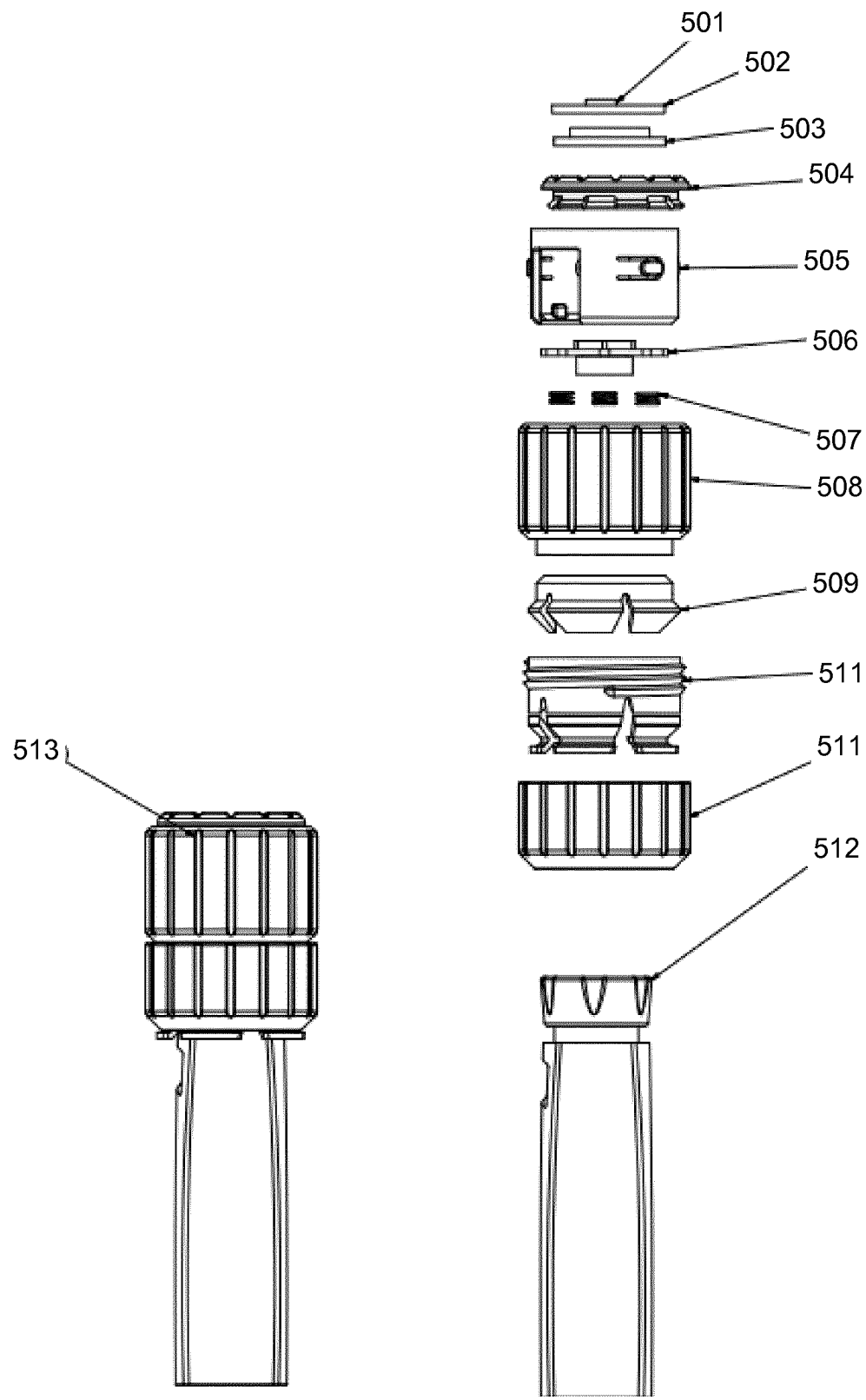
FIG. 5a and 5b show non-exploded and exploded views, respectfully, of a representative assembly of a device.

FIG. 5b shows an exploded view of a further assembly of the device and FIG. 5a shows this assembly in non-exploded form mounted to an insulin pen. As sown, the assembly comprises a positive power part 501 and a negative power ring 502 that allows charging of the rechargeable battery. A translucent portion 503 is provided so that LED light can be transmitted and seen from outside. A top button part 504 is provided which in operation is pressed by the user. The device further comprises a core portion 505 for holding the electronic components and sensors. A ring portion 506 is the encoder, this allows to know the number of insulin units injected. The ring portion 506 is placed on springs 507 which help to fix the encoder. The device further comprises a main body protection 508. Plastic holding portions 509, 510 and 511 are for holding e.g. an insulin pen, once the device is attached to the insulin pen. The parts denoted by reference signs 501 to 505 are freely rotatable versus the parts denoted by reference signs 506 to 511 that are attached to the insulin pen. When the patient injects insulin, the rotation amount allows to know the dosage injected.

Figure 6:
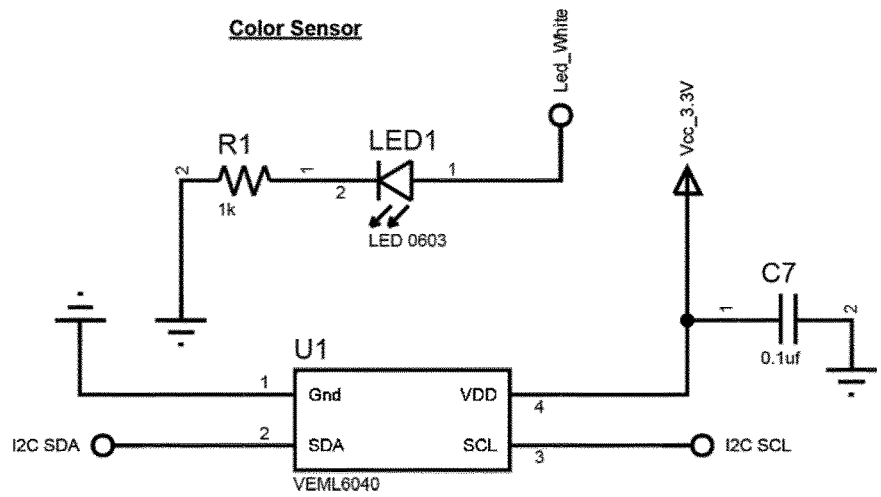
FIG. 6 shows an example circuit for a colour sensor.

FIG. 6 shows an example circuit for a colour sensor, exemplarily shown is a RGBW Color Sensor with I2C Interface—VEML6040A30G. The color sensor senses red, green, blue, and white light and incorporates photodiodes, amplifiers, and analog/digital circuits into a single chip using CMOS process. As shown, the circuit includes and LED that is mounted in the device such that when the device is mounted to the insulin pen, light from the LED shines on a colour coded portion of the insulin pen (e.g. the pushbutton). The sensor is adapted to detect, i.e. mounted at the devices such it can detect the colour of the coding. The colour sensor is coupled to the processing means such that the processing means can detect the type of insulin in the insulin pen. The sensor is connected to the device such that the device can detect the type of insulin at the time of application. As at the time of application the pushbutton 101 is fully depressed, for example a focussing lens for concentrating light from the LED onto the colour coded portion is provided at the device at a distance with respect to the LED optimized for the configuration of the depressed pushbutton, i.e. when the LED is closest to the colour coding provided typically at the pushbutton. This allows for optimum illumination of the colour coding and thus for a reliable colour detection. Even though detection of the kind of insulin is possible for a large number of used insulin types in view of a general standardized colour coding applied for insulin, as the skilled person will understand, the same principle is in general also applicable for further drugs when a corresponding color coding system is implemented either specifically to be used with the device or generally.

Figure 7:
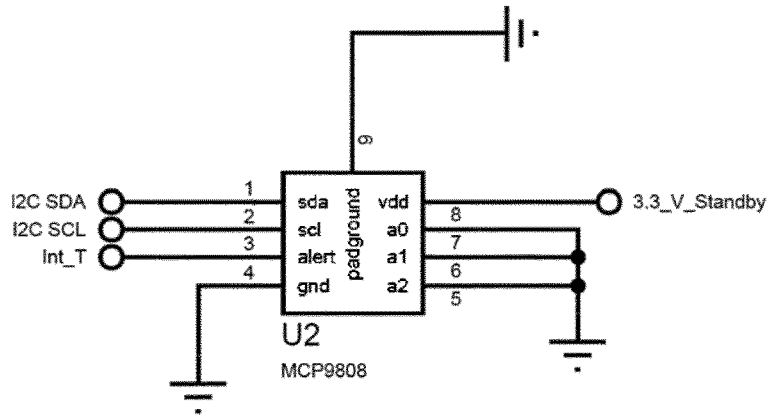
FIG. 7 shows an example of a digital temperature sensor.

FIG. 7 shows an example of a digital temperature sensor which allows for measuring of the insulin temperature at steps of plus/minus 0.5° C. The sensor is adapted to measure the temperature of the portion of the pen holding the insulin. It was found that only a very small—not significant—difference exists between the sensed temperature and the actual insulin temperature which can easily be dealt with, e.g. by a small calibration.

Figure 8:
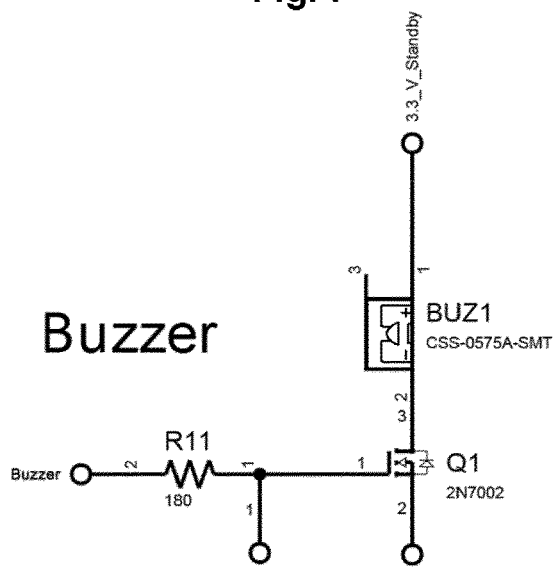
FIG. 8 shows an exemplam circuit for a buzzer.

FIG. 8 shows an exemplary circuit for a "buzzer", i.e. for an alarm usable with a device of the present invention. This buzzer is a transductor and allows for outputting different sound alarms with different tone colours, e.g. to warn a user in the case that a used insulin pen becomes empty. The buzzer allows in combination with RGB LEDs shown in the following figure to output various alarms to the patient as described above.

Figure 9:
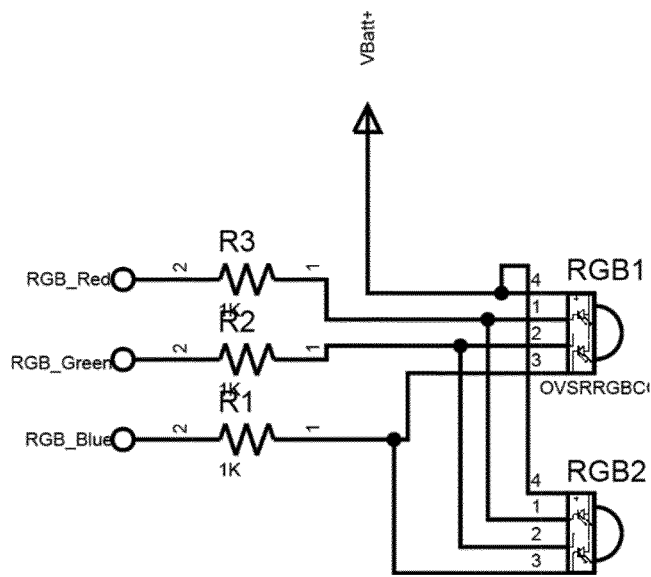
FIG. 9 is an exemplary circuit for controlling RGB LEDs to display visual alarms.
Figure 10A:
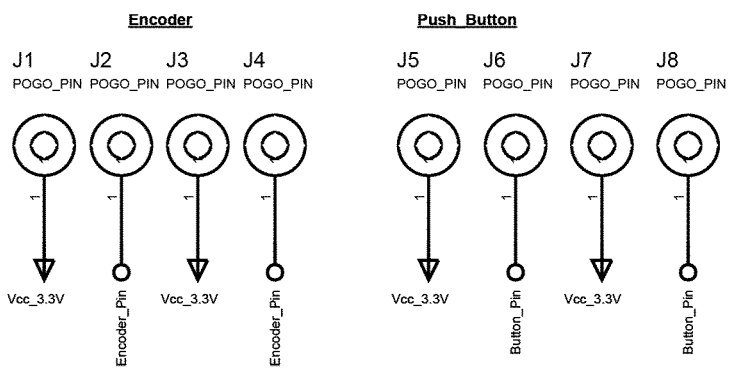
FIGS. 10a and 10b show example detectors.
Figure 10B:
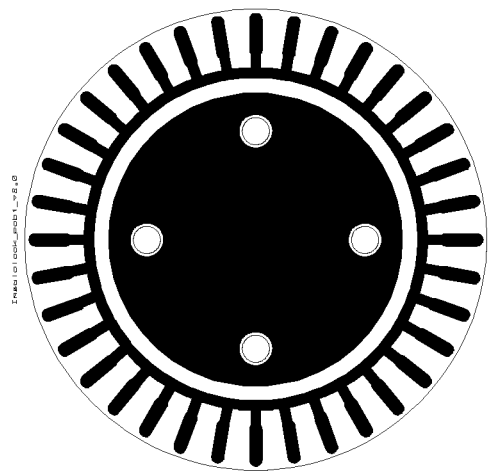

As the skilled person can derive from FIG. 9, the circuitry is circuitry for controlling RGB LEDs to display visual alarms in red, green orange and blue colours (or in mixtures thereof). FIGS. 10a and 10b show example detectors for detecting the rotation of a ring actuator provided at the device to be turned by the user to adjust the dosage e.g. of insulin to be applied. FIGS. 10a and 10b show the encoder system. As the skilled person will understand from the circuit diagrams, electrical pulses are detected which are generated when the pogo pins (FIG. 10a) physically make contact with the encoder printed circuit board (FIG. 10b). By adjusting the encoder PCB, the degree sensitivity can be adjusted. The printed circuit board (PCB) of FIG. 10b can be attached to the ring actuator of the pen. As the skilled person can derive from FIGS. 10a and 10b, when the PCB is rotated in relation to the electronics shown in FIG. 10a, the degree of rotation of the ring actuator can be detected e.g. to be stored in the dataset.

Figure 11:
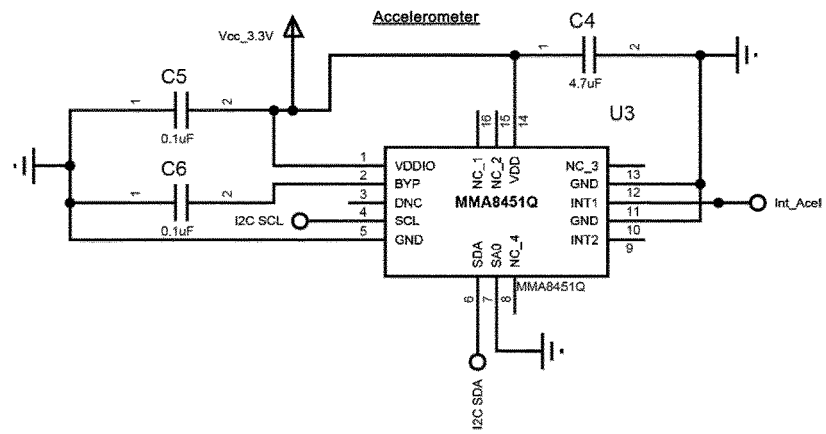
FIG. 11 shows exemplam circuitm for pen orientation angle detection means.

FIG. 11 shows exemplary circuitry for a pen orientation angle detection means, i.e. for a sensor adapted to detect an angle of orientation of a pen to which the device according to the invention is mounted. As the skilled person will understand from the shown circuitry, this example corresponds to a 3-axis, 14-bit/8-bit, digital accelerometer for determining the 3D orientation of the pen in space. This accelerometer enables verification if the patient is purging the pen or injecting the insulin into the body.

Figure 12:
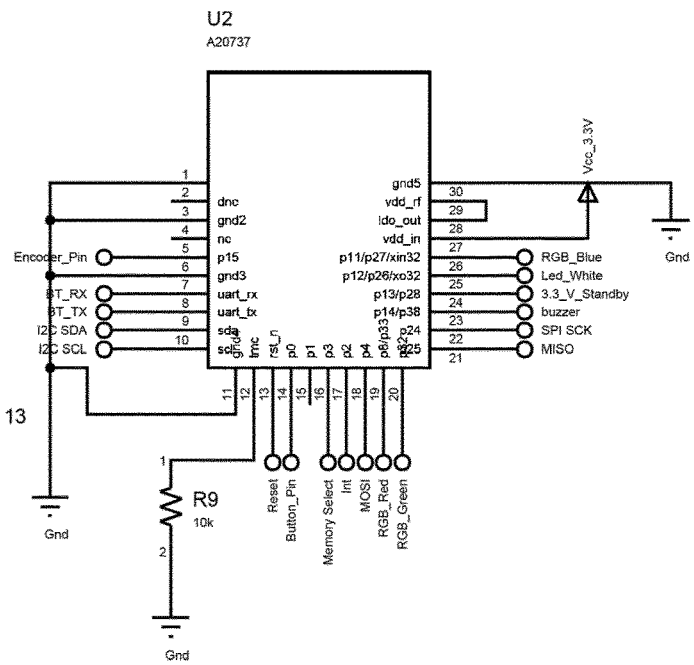
FIG. 12 shows example circuitm for wireless communication means.

FIG. 12 shows example circuitry that may be used for realizing wireless communication means. As the person skilled in the art can derive from the shown diagram, the shown circuitry allows for enabling Bluetooth communication between the installation and an external device. The circuitry enables sending data from the device to an application installed on the external device and to a cloud storage such that multiple external devices can be kept synchronized with data stored in the data cloud.

Figure 13:
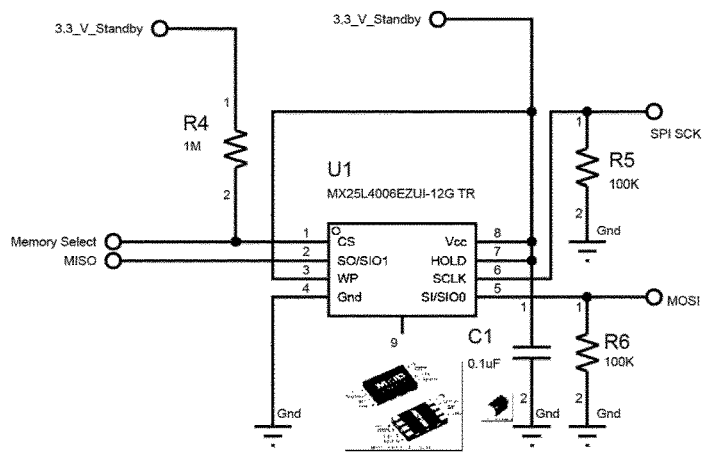
FIG. 13 shows example circuitm for storage means.

FIG. 13 shows example circuitry that may be used for realizing a storage means e.g. at an external device. The shown storage is of particular advantage as it enables storing data for a time span of up to one year.

The circuits shown in FIGS. 6 to 13 described above turned out to be of particular advantage for the present device as they allow to be provided in combination in the device of the invention while the device can be realized as a small device to be removably coupled to a standard pen such as an insulin pen while it can be handled conveniently by a patient.

The inventors found that for example, the color sensor implemented exemplarily as RGBW Color Sensor with I2C Interface—VEML6040A3OG turned out to be advantageous for detection of brand and kind of insulin. According to the brand or kind, the step of rotation of a dosage actuator provided at an insulin pen will be different for dosage of each shot. The dosage detection means exemplarily implemented as the combination of 4× Single Pogo Pin contact—AVX 709150001025006 with PCB 01 turned out to be advantageous for the detection of dosage. Rotation of the dosage actuator, i.e. the injector charger (with RGB color kind insulin previously detected) turned over the PCB 01 advantageously enables determination of the angle of rotation which in combination with the pen allows to determine the dosage. For example, 18 degrees of rotation corresponds to 1 unit in the case of Kwikpen, Flexpen and Solostar which are pens known to the person skilled in the art. In the case of Flextouch which is a further pen known to the skilled person, 15 degrees corresponds to 1 unit. This information in combination with the type and brand of insulin previously detected, generates the amount injected.

By incorporating dedicated sensors into the device, it became possible to ensure compatibility with various pens such as e.g. Insulclok, Kwikpen, Flexpen, Solostar and Flextouch. Achieving this goal has been a challenge which was solved by the inventors by the provision of a combination of different sensors, specific software and calibration.

Operation

The operation of the device (1) of the invention in any configuration is now briefly disclosed. As mentioned above, any data read or write operation by the patient may be carried out using an application installed in an external device, such as a smartphone, tablet or computer, in communication with the device (1) of the invention.

As a first step for using the device, the patient inputs his/her basic personal data, as well as, in the case of using the application, a user and password. Next, he/she can input any alarms needed. For example, in case a patient in particular must carry out three injections a day, he/she inputs what time he/she wishes to be reminded for said injections. Also the patient can fill the data from the caregiver, name, phone number and email address to send alerts about the use of the insulin pen and follow the treatment easily. Data and parameters may be input by the patient e.g. using a mobile device connected wirelessly with the device. The information is stored in the storing means of the device and, thanks to the control clock, i.e. the real time clock, the alarm means is actuated at the above specified time. The patient then carries out the injection. After the injection, which is automatically detected by the device and in a preferred embodiment also the kind of insulin and dosage is detected, said device requires the patient to input the volume of insulin injected, the glucose level in blood, and input this data e.g. using a corresponding application or software installed on a smartphone or tablet. These data are so stored in the storing means of the device for the generation of graphs. The device goes back to wait mode until the time of the next injection. As described above, various sound and visual alarms can be output to advise the patient in the case of an error or in the case of correct application.

Further, the patient may view the information transferred from the device to an external device, such as graphs showing the glucose level in blood and the injection times, at any time. The application may additionally send all the information automatically to an external server allowing for the corresponding doctor to view patient data.

The invention claimed is:

1. A device for monitoring the application of a drug to a patient by means of a drug pen, whereby the drug pen comprises a front end provided with an injection needle and a rear end provided with an actuation pushbutton, comprising:
   a body which can be dismountably coupled to the drug pen, whereby the body comprises:
   an essentially frustoconical gasket having an orifice configured for housing therein the actuation pushbutton of the drug pen;
   a coupling portion having a through orifice configured for housing the gasket therein such that a compression of said gasket takes place for compressing it firmly around the actuation pushbutton;
   a cover portion configured for coupling to the coupling portion;
   an injection detection means implemented as an actuation detector, whereby the actuation detector is a mechanical button provided in the cover portion, configured for detecting a pushing action such that the injection detection means is configured to determine when a drug injection is carried out by detecting the pushing action; and a processing means configured for storing the date and time of the drug injection when the drug injection detection means detects that a drug injection is carried out, wherein:

the processing means is adapted to store a dataset including the time and date of the drug injection;

the device comprises means for monitoring, at the time of application, the temperature of the drug, and the processing means is adapted to store this temperature into the dataset and whereby the device further comprises alarm means adapted to warn a user of the pen in the case that the detected drug temperature is above or below a preset threshold and if no or a wrong dose is applied or the drug injection is uncompleted and when the drug injection is completed to confirm such correct application;

the device further comprises one or more accelerometers adapted to detect the three dimensional orientation of the drug pen when the device is mounted to the drug pen, whereby the processing means is adapted to store the three dimensional orientation of the drug pen into the data set;

the device further comprises a drug kind detection means comprising a color sensor and being adapted to automatically detect the kind of applied drug when a drug injection is detected, whereby the kind of drug is identified via a color label provided at the pushbutton of the pen, and whereby the processing means is adapted to store the detection result of the drug kind detection means into the dataset; and the pushbutton to which the body of the device is coupled, before being actuated, is retracted by turning it backwards a distance in proportion to a drug dose to be injected, as the user turns the pushbutton, an indication window shows the user a number of drug units that is being charged for injection.

2. The device according to claim 1, wherein the drug kind detection means further comprises a light emitting diode (LED), the LED being adapted to emit light such that corresponding light reflected from the color label provided at the drug pen is sensed by the color sensor to detect the kind of drug, based on the color label.

3. The device according to claim 2, wherein the drug is insulin.

4. The device according to claim 1, wherein the alarm means is for warning the patient of predetermined events.

5. The device according to claim 4, wherein the device comprises a battery charge state detector, wherein the alarm means is adapted to output an alarm based on a detection result of the battery charge state detector, when the charge state is below a predetermined threshold.

6. The device according to claim 1, wherein the device further comprises a dosage detection means adapted to detect the amount of charged drug based on a setting of a dosage actuator of the drug pen, wherein the processing means is adapted to store the applied dosage into the dataset based on a detection result of the dosage detection means.

7. The device according to claim 1, wherein the device comprises a control clock adapted to output the date and the time of day to the processing means.

8. The device according to claim 7, wherein the processing means is adapted to detect a time period after a preset date and time, based on an output of the control clock, and wherein the alarm means is adapted to output an alarm, when the processing means detects that the injection detection means has not detected an injection for a predetermined time period after a preset date and time.

9. The device according to claim 7, wherein the processing means is adapted to detect a predefined time period after the date and time of the injection, based on an output of the control clock, and wherein the alarm means is adapted to output an alarm if a further injection is detected within the predefined time period.

10. The device according to claim 1, further comprising a wireless communication means configured for communicating with at least one external device.

11. The device according to claim 10, wherein at least one external device is a user equipment.

12. The device according to claim 11, wherein the user equipment is a mobile phone.

13. The device according to claim 10, wherein at least one external device is an external server.

14. The device according to claim 10, wherein the wireless communication means is adapted to communicate with the user equipment via Machine to Machine communication.

15. The device according to claim 14, wherein the Machine to Machine communication is Bluetooth.

16. The device according to claim 10, wherein the wireless communication means is adapted to communicate with the at least one server via a general network.

17. The device according to claim 15, wherein the general network is the internet.

18. A method for the operation of the device according to claim 1 for monitoring the application of a drug to a patient by means of a drug pen, comprising the following steps:

detecting, by an injection detection means of the device, when a drug injection is carried out;

storing the date and time of the drug injection when the injection detection means detects that the drug injection is carried out;

storing, in a dataset, the date and time of the drug injection, an orientation of the drug pen at the time of the drug injection, the temperature of the drug at the time of the drug injection, and the detection result of the drug kind detection means;

communicating the dataset to an external device; and providing a person, through an application in the external device, information based on the dataset.

19. The method according to claim 18, wherein the drug is insulin.

20. A system comprising the device according to claim 1, further comprising at least one external server, the device being adapted to communicate with the at least one external server such that the dataset is stored on the external server via a general network when an injection is detected.

21. The system according to claim 20, wherein the processing means is adapted to detect a time period after a preset date and time, based on an output of a control clock, and wherein the alarm means is adapted to output an alarm, when the processing means detects that the injection detection means has not detected an injection for a predetermined time period after a preset date and time, whereby the alarm means and a wireless communication means are adapted such that, the alarm is communicated to the at least one external server which in turn is adapted to automatically send a message to a user equipment.

22. The system according to claim 20, wherein the general network is the internet.

23. The device according to claim 1, wherein the dataset further includes as a further parameter an applied dose of drug at the time of application.

24. The device according to claim 1, wherein the drug is insulin.

\* \* \* \* \*